(12) United States Patent
Hill et al.

(10) Patent No.: US 11,627,969 B2
(45) Date of Patent: Apr. 18, 2023

(54) APPARATUS AND METHODS FOR CLOSING VESSELS

(71) Applicant: VENOVATION INC., Santa Clara, CA (US)

(72) Inventors: Bradley B. Hill, Santa Clara, CA (US); James Hong, Sunnyvale, CA (US); Wenkang Qi, Cupertino, CA (US); Bryan Duenas, East Palo Alto, CA (US)

( * ) Notice: Subject to any disclaimer, the term of this patent is extended or adjusted under 35 U.S.C. 154(b) by 121 days.

(21) Appl. No.: 16/697,087

(22) Filed: Nov. 26, 2019

(65) Prior Publication Data
US 2020/0170644 A1    Jun. 4, 2020

Related U.S. Application Data

(60) Provisional application No. 62/772,045, filed on Nov. 27, 2018.

(51) Int. Cl.
*A61B 17/122* (2006.01)
*A61B 17/128* (2006.01)

(52) U.S. Cl.
CPC ........ *A61B 17/122* (2013.01); *A61B 17/1285* (2013.01)

(58) Field of Classification Search
CPC .......... A61B 2017/1225; A61B 17/122; A61B 17/1285; A61B 17/128; A61B 17/10; A61B 17/11; A61B 17/1222; A61B 17/1227
See application file for complete search history.

(56) References Cited

U.S. PATENT DOCUMENTS

| | | | |
|---|---|---|---|
| 8,945,177 B2 * | 2/2015 | Dell | A61B 17/10 606/213 |
| 2015/0201947 A1 * | 7/2015 | Hill | A61B 17/12031 606/157 |
| 2017/0095257 A1 * | 4/2017 | Miller | A61B 17/0643 |

* cited by examiner

*Primary Examiner* — Brooke Labranche
(74) *Attorney, Agent, or Firm* — William A. English; Vista IP Law Group LLP

(57) ABSTRACT

Apparatus and methods are provided for closing a tubular structure within a patient's body. The apparatus includes a needle including a proximal end including a hub, a distal end including a sharpened distal tip, a lumen having an oblong cross-section extending proximally from the distal end, and defining a longitudinal axis between the proximal and distal ends, and a clip deliverable from the lumen. The clip is compressible between a relaxed state in which a plurality of tines of the clip are shaped to engage and close a tubular structure within a patient's body, and a stressed state in which the tines are compressed to allow the clip to be loaded into the. The apparatus may also include a pusher member for deploying the clip from the distal tip of the needle such that the tines engage and close a tubular structure through which the tubular member is directed.

24 Claims, 6 Drawing Sheets

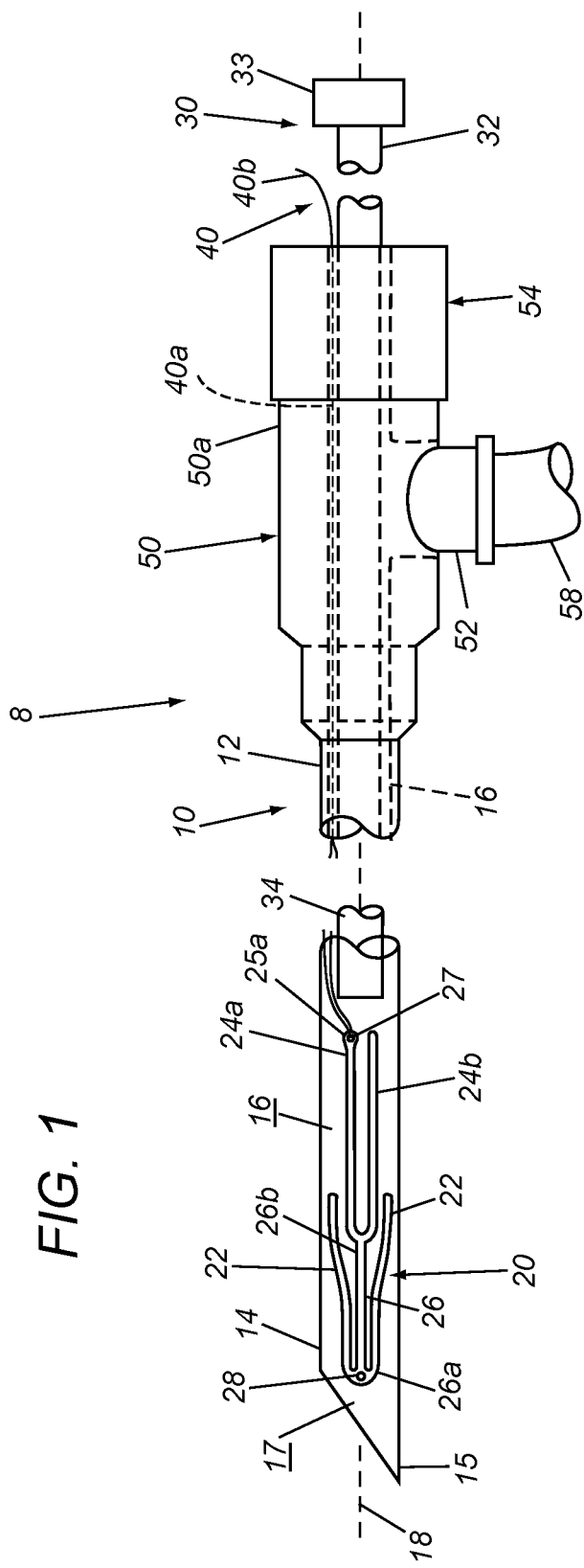

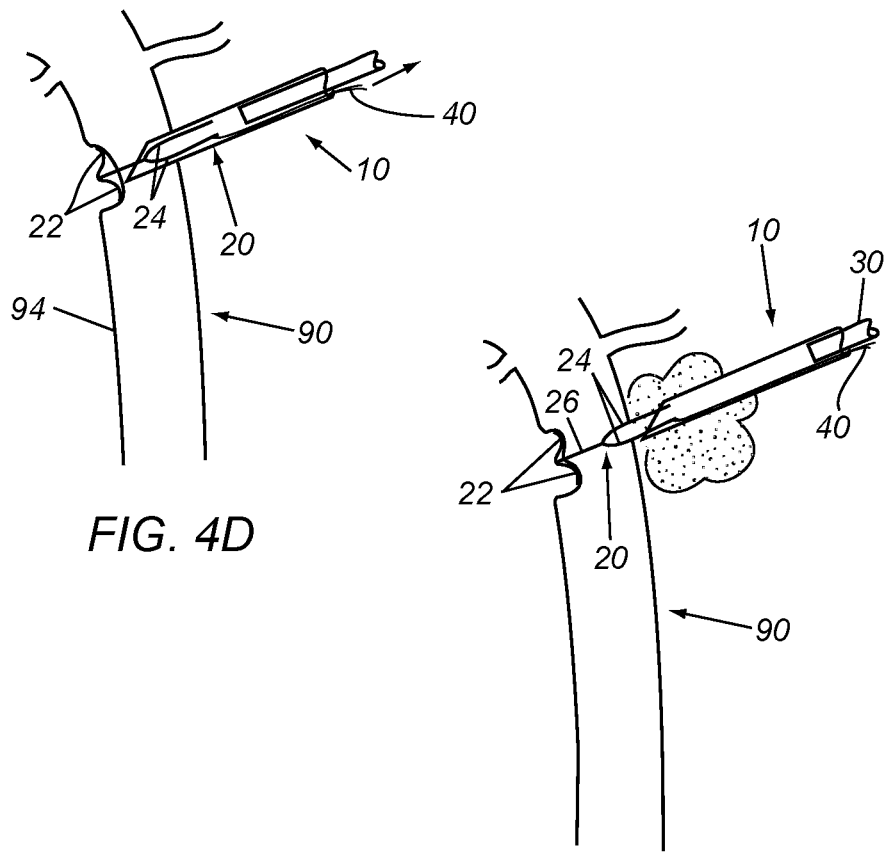
FIG. 4D
FIG. 4E
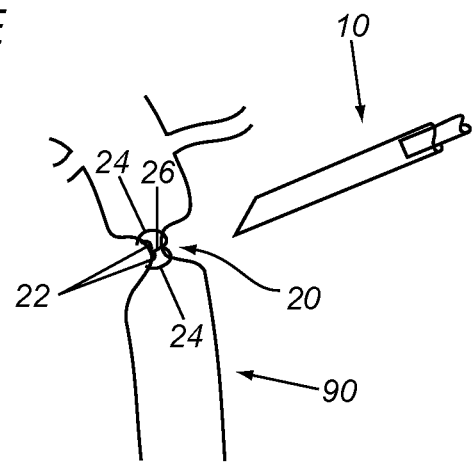
FIG. 4F

APPARATUS AND METHODS FOR CLOSING VESSELS

RELATED APPLICATION DATA

The present application claims benefit of provisional application Ser. No. 62/772,045, filed Nov. 27, 2018, and is related to co-pending U.S. application Ser. No. 14/606,892, filed Jul. 23, 2015, which is a continuation of International Application No. PCT/US2013/052432, filed Jul. 27, 2013, which claims the benefit of U.S. provisional application Ser. No. 61/676,551, filed Jul. 27, 2012, the entire disclosures of which are expressly incorporated by reference herein.

FIELD OF THE INVENTION

The present invention relates to apparatus, systems, and methods for closing blood vessels or other tubular structures within a patient's body. More particularly, the present invention relates to apparatus and methods for closing veins or other tubular structures in a patient's body, e.g., by delivering one or more clips into, through, and/or around the tubular structure.

BACKGROUND

Mild vein-related abnormalities are common and affect most adults. More severe disease with visible varicose veins occurs in up to forty percent (40%) of men and women. Chronic venous insufficiency occurs in about two percent (2%) of the U.S. population and can cause swelling, stasis pigmentation, scarring of the skin and underlying tissues, and skin ulceration in advanced cases. The incidence of all venous disease increases with advancing age.

The causes of varicose vein disease are varied. A family history is common and a genetic predisposition may play a factor. Obstruction of the main draining veins of the leg due to blood clots, called deep venous thrombosis or DVT, and loss of valve function or "valvular incompetence" are the main causes of varicose veins and most forms of venous insufficiency.

Patients with advanced disease are often unable to continue their customary employment, and they may become temporarily or permanently disabled from lack of mobility. The economic and psychological effects can be profound for these patients.

Patients who have varicose veins or more serious forms of venous insufficiency caused by valvular incompetence of the saphenous vein can be managed in a variety of ways. The first line of therapy in most cases is compression therapy and leg elevation. These noninvasive measures can help alleviate symptoms and heal ulcers in some instances. Oftentimes, patients are unable to tolerate tight compression garments and they may not be able to elevate the extremity for an adequate time to relieve symptoms and promote ulcer healing because of work requirements and/or other lifestyle issues.

Invasive treatment methods for disease stemming from valvular incompetence of the saphenous vein include: 1) vein stripping, 2) high-ligation, 3) foam sclerotherapy, and 4) endo-venous ablation. Vein stripping and high-ligation have fallen out of favor because stripping is traumatic and high-ligation is associated with a high recurrence rate. Foam sclerotherapy has not had widespread adoption and is known to cause visual disturbance (scotoma), migraine-like headache, cough, and neurologic deficit (usually transient) in less than two percent (2%) of cases.

In recent years, endo-venous ablation using radiofrequency energy or laser energy has become the preferred treatment for patients who suffer from venous disease due to axial reflux in the long and short saphenous veins and in some cases involving reflux in the perforating veins. However, endo-venous ablation requires tumescent anesthesia and is typically done in an ambulatory surgery setting. Even though the procedure is minimally invasive, some patients experience significant bruising and post-procedural pain, which may last for more than a week. Endo-venous ablation involves destruction of the vein from the inside out along the full length of the treatment segment. The tissue destruction causes pain in the soft tissues after the anesthetic wears off. Some patients require prescription pain medications and often several days off work until the pain has resolved.

Therefore, there is a need for improved systems for treating venous insufficiency caused by valvular incompetence of the saphenous vein.

SUMMARY

The present invention is directed to apparatus, systems, and methods for closing a tubular structure, e.g., a blood vessel, such as a saphenous or other vein, to eliminate flow of fluid through the lumen of the tubular structure. In addition, the present invention is directed to apparatus, systems, and methods for delivering one or more clips into a patient's body, e.g., percutaneously, to close tubular structures.

The description herein focuses on using various apparatus and methods to close a saphenous vein, e.g., for treatment of valvular incompetence. It will be appreciated that other tubular structures may also be closed using the apparatus and methods described herein. For example, other structures that may be treated include arteries, biliary tubes, bronchial or other airway tubes, or other anatomical structures, including prosthetic tubular grafts, e.g., as are used in vascular bypass operations.

In accordance with an exemplary embodiment, an apparatus is provided for closing a tubular structure within a patient's body that includes a tubular member comprising a proximal end including a hub, a distal end including a sharpened distal tip to allow insertion into tissue through a tubular structure, and a lumen extending proximally from the distal end; a clip loaded in the lumen, the clip compressible between a relaxed state in which a plurality of tines of the clip are shaped to engage and close a tubular structure within a patient's body, and a stressed state in which the tines are compressed to allow the clip to be loaded into the lumen, at least one of the tines including an eyelet; a release wire including first and second ends positioned adjacent the hub and an intermediate region passing through the lumen and the eyelet; and a pusher member comprising a proximal end and a distal end sized for advancement within the lumen for at least partially deploying the clip from the distal tip of the needle such that the tines engage and close a tubular structure through which the tubular member is directed.

In accordance with another embodiment, an apparatus is provided for closing a tubular structure within a patient's body that includes a) a clip comprising i) a central region including a proximal end and a distal end, the distal end including a hole for receiving a loading wire; ii) a pair of distal tines extending from the distal end, the distal tines biased to extend away from one another in a relaxed state; and iii) a pair of proximal tines extending from the proximal end, the proximal tines having a length greater than a length of the distal tines, the proximal tines defining loops in a relaxed state that at least partially surround respective distal tines within a plane, one of the proximal tines including an eyelet adjacent a tip thereof; and b) a delivery device comprising i) a tubular member comprising a proximal end including a hub, a distal end including a sharpened distal tip such that the tubular member may be directed into tissue through a tubular structure within a patient's body, and a lumen extending proximally from an outlet in the tubular member distal end, the clip loaded within the lumen in a stressed state wherein the proximal tines and distal tines are substantially straightened and axially aligned with the central region; ii) a pusher member within the lumen movable relative to the tubular member from a first position to a second position to deploy the distal tines initially from the outlet, the distal tines resiliently returning towards the relaxed state; and iii) a release wire including first and second ends and an intermediate region received through the eyelet, the release wire actuatable to direct the clip proximally relative to the tubular member distal end to engage the distal tines with the tubular structure, the release wire is removable from the eyelet to allow the proximal tines to be deployed from the lumen, whereupon the proximal tines resiliently return towards the relaxed state to at least partially surround and close the tubular structure.

In accordance with still another embodiment, a clip is provided for closing a tubular structure within a patient's body that includes a central region including a proximal end and a distal end, the distal end including a hole for receiving a loading wire; a pair of distal tines extending from the distal end, the distal tines biased to extend away from one another in a relaxed state; and a pair of proximal tines extending from the proximal end, the proximal tines having a length greater than a length of the distal tines, the proximal tines defining loops in a relaxed state that at least partially surround respective distal tines within a plane, one of the proximal tines including an eyelet adjacent a tip thereof, the clip configured to be loaded within a delivery device in a stressed state wherein the proximal tines and distal tines are substantially straightened and axially aligned with the central region, the proximal tines and distal tines biased to the relaxed state.

In accordance with another embodiment, a method is provided for closing a tubular structure within a patient's body, e.g., a vein, that includes inserting a distal tip of a delivery device into the patient's body into-and-through a tubular structure, the delivery device carrying a clip including a set of distal tines and a set of proximal tines in a stressed state and a release wire coupled to one of the proximal tines; partially deploying the clip such that the distal tines of the clip extend from the distal tip beyond the tubular structure and elastically deform towards a relaxed state; actuating the release wire to direct the distal tines proximally into engagement with the tubular structure; disengaging the release wire from the one of the proximal tines; and fully deploying the clip from the lumen such that the proximal tines are released from the distal tip and elastically deform to at least partially surround and close the tubular structure.

In accordance with still another embodiment, a method is provided for closing a blood vessel within a patient's body that includes inserting a distal tip of a delivery device into the patient's body into-and-through the blood vessel, the delivery device carrying a clip including a set of distal tines and a set of proximal tines in a stressed state and a release wire coupled to one of the proximal tines; partially deploying the clip such that the distal tines of the clip extend from the distal tip beyond the tubular structure and elastically extend away from one another to a deployed configuration; directing the distal tines in the deployed configuration proximally into engagement with a distal side of the blood vessel; disengaging the release wire from the one of the proximal tines; and fully deploying the clip from the lumen such that the proximal tines are released from the distal tip and elastically deform to at least partially surround and close the blood vessel.

In accordance with yet another embodiment, a method is provided for loading a clip into a delivery device that includes providing a delivery device including a tubular member comprising a proximal end, a distal end, and a lumen extending between an opening in the proximal end and an outlet in the distal end, and providing a clip in a relaxed state comprising a central region including a proximal end and a distal end, the distal end including a hole for receiving a loading wire, a pair of distal tines extending from the distal end, the distal tines biased to extend away from one another in the relaxed state, and a pair of proximal tines extending from the proximal end, the proximal tines having a length greater than a length of the distal tines, the proximal tines defining loops in the relaxed state that at least partially surround respective distal tines within a plane. The clip is mounted to a loader in the relaxed state such that a pair of prongs are positioned within the loops, and a loading wire is directed through the hole and into the lumen. The loader is mounted to the proximal end of the tubular member such that the clip is disposed adjacent the opening, and the loading wire is manipulated to pull the clip through the opening into the lumen, thereby directing the proximal tines and distal tines to a stressed state where the proximal tines and distal tines are at least partially straightened and aligned with the central region. Thereafter, the loader may be removed from the proximal end of the tubular member, and the loading wire may be removed from the hole and lumen. optionally, a pusher member may be coupled to the proximal end of the tubular member such that the pusher member is disposed within the lumen adjacent the clip such that subsequent advancement of the pusher member deploys the clip at least partially from the outlet.

Other aspects and features of the present invention will become apparent from consideration of the following description taken in conjunction with the accompanying drawings.

BRIEF DESCRIPTION OF THE DRAWINGS

These and other features, aspects, and advantages of the present disclosure will become better understood with regard to the following description, appended claims, and accompanying drawings where:

FIG. 1 is a partially cross-sectional side view of an exemplary embodiment of an apparatus including a needle, plunger, and an occlusion clip deployable from the needle.

FIG. 1A is an exemplary cross-sectional view of a needle of the apparatus of FIG. 1, taken along line 1A-1A.

FIGS. 4A-4F are cross-sectional views of a patient's body, showing an exemplary method for closing a blood vessel using the apparatus of FIG. 1.

DETAILED DESCRIPTION OF THE EXEMPLARY EMBODIMENTS

Figure 2A:
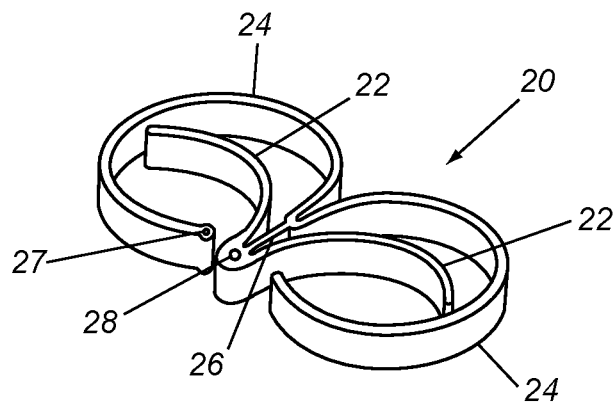
FIGS. 2A-2C are perspective, side, and end views, respectively of exemplary embodiments of an occlusion clip that may be delivered using the apparatus of FIG. 1.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Turning to the drawings, FIG. 1 shows an exemplary embodiment of an apparatus 8 for delivering a clip 20 into a patient's body, e.g., to close a tubular structure, such as a saphenous vein or other blood vessel. Generally, the apparatus 8 includes a needle or other tubular member 10, one or more clips 20 (one shown), a pusher member 30, and a release wire 40. Optionally, the apparatus 8 may be part of a system, e.g., including one or more other components to facilitate delivering the clip, such as a source of fluid, an ultrasound transducer and/or other imaging device, a needle guide, and the like (not shown).

The needle 10 may be a substantially rigid tubular member, e.g., a section of hypo-tube, including a proximal end 12 with a hub 50, a distal end 14, and a lumen or slot 16 extending at least partially between the proximal and distal ends 12, 14, thereby defining a longitudinal axis 18 between the proximal and distal ends 12, 14. The hub 50 may have a size and/or shape to allow the apparatus 8 to be held and/or manipulated during use. The hub 50 may be substantially permanently attached to the proximal end 12 of the tubular body 10, e.g., by one or more of bonding with adhesive, sonic welding, interference fit, cooperating connectors (not shown), and the like. As shown, a clip 20 may be loaded within the lumen 16 adjacent the distal end 14, and the pusher member 30 may be disposed at least partially within the lumen 16. The distal end 14 of the needle 10 may terminate in a beveled, pointed, or other sharpened distal tip 15, e.g., to facilitate percutaneous introduction of the needle 10 directly through tissue to a target location within a patient's body and includes an outlet 17 communicating with the lumen 16 from which the clip 20 may be deployed, as described further below. Alternatively, the distal end 14 may have a blunt shape (not shown) and the needle 10 may be directed into tissue through another needle, trocar, or other device (also not shown).

In one embodiment, as shown in FIG. 1A, the lumen 16 may have a rectangular shape, an oval shape, or other oblong shape, e.g., including a major axis "M" and a smaller minor axis "m," e.g., such that the clip 20 may be loaded into the lumen 16 in a predetermined orientation about the longitudinal axis 18 of the needle 10. As used herein, "oblong" refers to any cross-sectional shape that includes a major axis that is larger than a minor axis and is configured to slidably receive one or more clips 20 therein while constraining the clip(s) 20 in a stressed state, as described further below.

In the embodiment shown in FIG. 1, a single clip 20 is provided within the lumen 16. Alternatively, a needle may be provided that includes a plurality of clips within the lumen, e.g., spaced apart axially from one another (not shown), such that multiple clips may be deployed sequentially from the needle. Exemplary embodiments of such needles are disclosed in U.S. Publication No. 2015/0201947, the entire disclosure of which is expressly incorporated by reference herein.

Generally, each clip 20 includes one or more pairs of tines or extensions thereon for engaging tissue, e.g., a wall of a vein or other tubular structure within a patient's body, as described further elsewhere herein. The clip 20 may be compressible between a relaxed state in which the tines are shaped to engage and/or close a tubular structure within a patient's body, and a stressed state in which the tines are compressed to allow the clip 20 to be loaded into the lumen 16 of the needle 10. Tips of the tines may have rounded, blunt, bulbous, or other atraumatic shapes, e.g., to allow engagement without penetrating or tearing tissue. Alternatively, the tips of the tines may be sharpened, beveled, barbed, or otherwise configured to facilitate introduction through tissue and/or engagement with the wall of the tubular structure being closed.

Figure 2B:
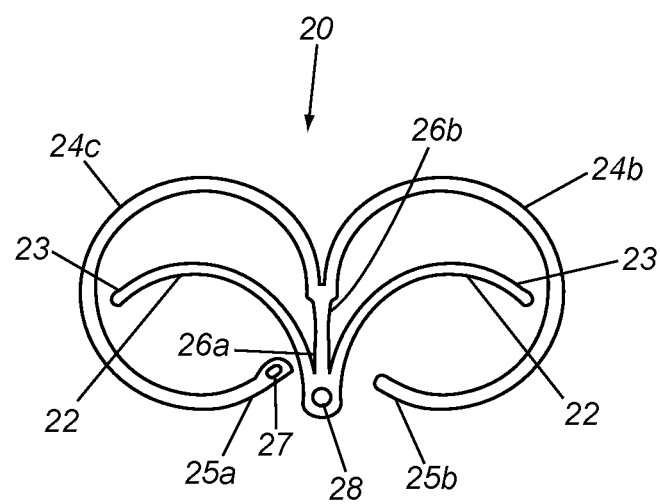
Figure 2C:
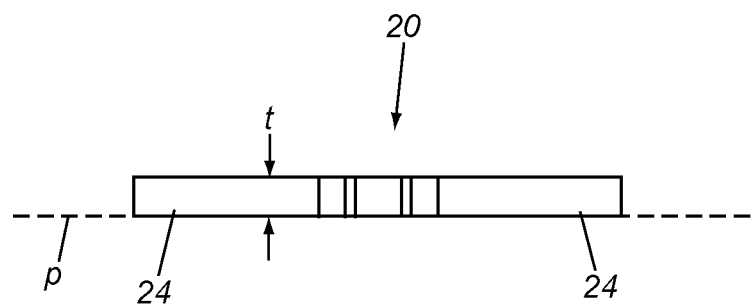

Turning to FIGS. 2A-2C, an exemplary embodiment of a clip 20 is shown in a relaxed state that includes two pairs of tines or extensions 22, 24 on opposite ends of an elongate central region 26, all lying within a common plane. As shown, the clip 20 includes a distal set of tines 22 extending from a distal or first end 26a of the central region 26 and a proximal set of tines 24 extending from proximal or second end 26b of the central region 26. In the relaxed state, the distal tines 22 are biased to extend away from one another, e.g., proximally and outwardly from the central region 26, for example, having a curved shape within the plane.

In the relaxed state, the proximal tines 24 define loops that at least partially surround respective distal tines 22 within the plane. As shown, the proximal tines 24 have a length greater than a length of the distal tines 22 such that the proximal tines 24 extend around the distal tines 22 and tips 25 of the proximal tines 24 are disposed adjacent the distal end 26a of the central region 26, e.g., on opposite sides of the distal end 26a. Consequently, tips 23 of the distal tines 22 are disposed within an open region defined within the proximal tines 24. As shown, one of the proximal tines 24a including an eyelet 27 adjacent a tip 25a thereof. The eyelet 27 may be sized to slidably receive a release wire (not shown in FIGS. 2A-2C) to facilitate manipulation of the clip 20 during delivery, as described elsewhere herein.

With additional reference to FIG. 1, the clip 20 is configured to be loaded within the lumen 16 of the needle 10 in a stressed state wherein the proximal tines and distal tines are compressed towards one another. For example, as shown in FIG. 1, the tines 22, 24 may be substantially straightened and axially aligned with the central region 26 within the plane, e.g., oriented towards proximally within the lumen 16 towards the hub 50 of the needle 10 when the clip 20 is loaded within the needle 10. However, once released from the lumen 16, the tines 22, 24 are biased to return automatically back towards the relaxed state.

The thickness of the clip 20 may be slightly less than the minor dimension "m" of the lumen 16, and the width of the tines 22, 24 and central region 26 within the plane may be slightly less than the major axis "M." Given the relative dimensions, the clip 20 may be slidably received in the lumen 16 with the tines 22, 24 maintained in the stressed state within the plane by the walls of the lumen 16. Optionally, the lumen 16 may provide sufficient clearance around the clip 20 to allow fluid to be delivered through the lumen 16 with the clip 20, or the lumen 16 include a longitudinal groove (not shown), e.g., in a wall of the major dimension to provide a path for fluid to travel through the lumen 16.

In an exemplary embodiment, the central region 26 may have a length between about one and four millimeters (1-4 mm), the distal tines 22 may have a length between about two and eight millimeters (2-8 mm), and the proximal tines 24 may have a length between about four and twelve millimeters (4-12 mm) (but longer than the distal tines 22). For example, the proximal tines 24 may have sufficient length to at least partially or entirely surround the outer wall of a vessel being occluded, e.g., a vein having a diameter between about four and fifteen millimeters (4-15 mm).

The clip 20 may be formed from an elastic or superelastic material, e.g., metal such as Nitinol or plastic, such that the tines 22, 24 may be compressed to facilitate loading the clip 20 into the needle 10 and resiliently biased towards the relaxed state to surround, penetrate, and/or otherwise engage a wall of a tubular structure and/or surrounding tissue to close the tubular structure. Alternatively, the clip 20 may be formed from shape memory material, e.g., that may be loaded into the needle 10 in a first state, e.g., a martensitic state at a first temperature below body temperature, and may be deployable from the needle 10 in a second state, e.g., an austenitic state at body temperature in which the clip 20 may remember an engagement shape for closing the tubular structure. For example, the clip 20 may be cut or otherwise formed from a sheet of Nitinol or other superelastic metal, e.g., by laser cutting, stamping, machining, and the like, and heat treated and/or otherwise processed to set the shape of the relaxed state.

Turning to FIGS. 3A-3D, an exemplary method is shown for loading the clip 20 into a delivery device, such as the lumen 16 of the needle 10 shown in FIG. 1. Initially, the clip 20 may be formed and provided in the relaxed state, e.g., as shown in FIGS. 2A-2C. A release wire 40, e.g., an elongate flexible filament formed from suture material, metal wire, and the like, may be directed through the eyelet 27 such that the clip 20 is positioned at an intermediate location between opposite ends (not shown) of the release wire 40.

Figure 3A:
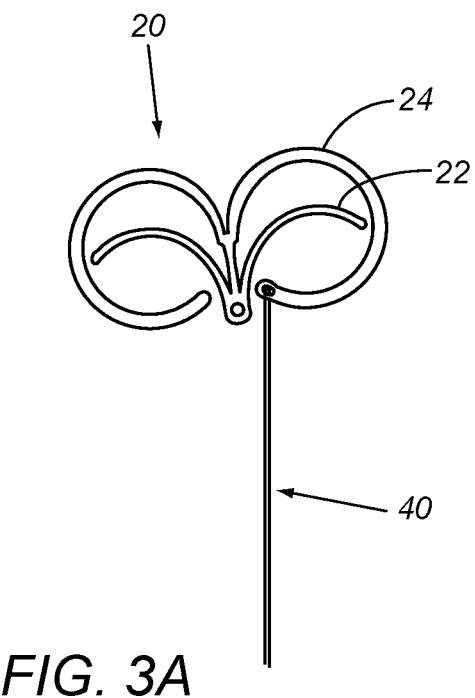
FIGS. 3A-3D show an exemplary method for loading an occlusion clip, such as the clip of FIGS. 2A-2C into a delivery device, such as the apparatus of FIG. 1.
Figure 3B:
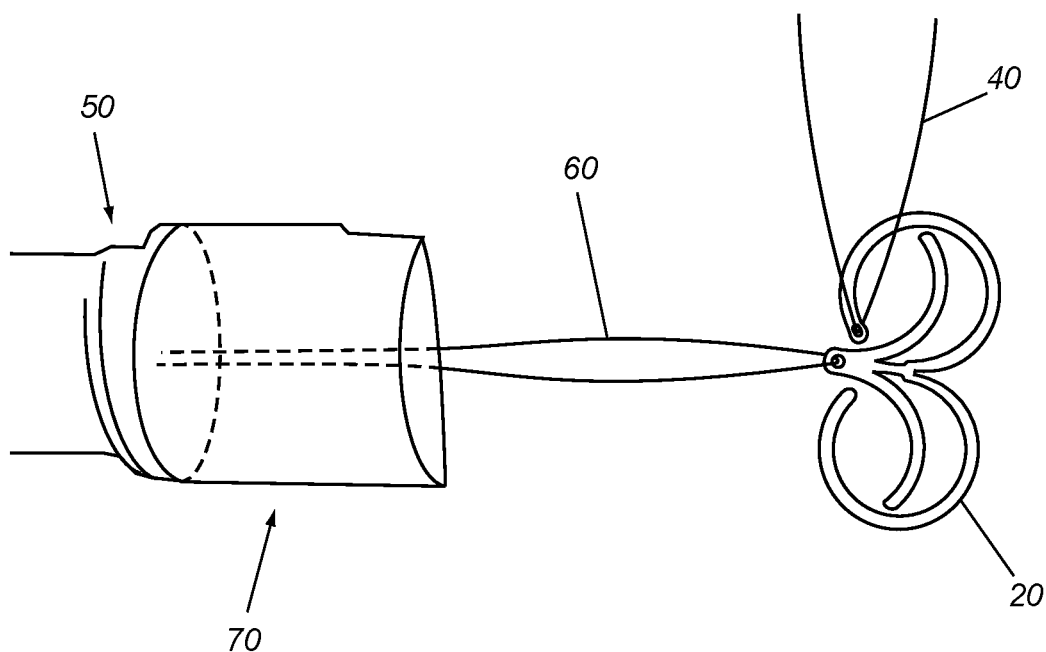

In addition, as shown in FIG. 3B, a pull or loading wire 60 and a loader structure 70 may be provided that may be used during the loading process and removed before final assembly, packaging, sterilization, and/or other manufacturing procedures. The loading wire 60 may be a flexible filament formed from suture material, metal wire, and the like sized to be received through the hole 28 in the clip 20 as well as the lumen 16 of the needle 10. During loading, one end of the loading wire 60 may be directed through the hole 28 in the clip 20, e.g., to position the clip 20 at an intermediate location between the ends (not shown) of the loading wire 60.

Figure 3C:
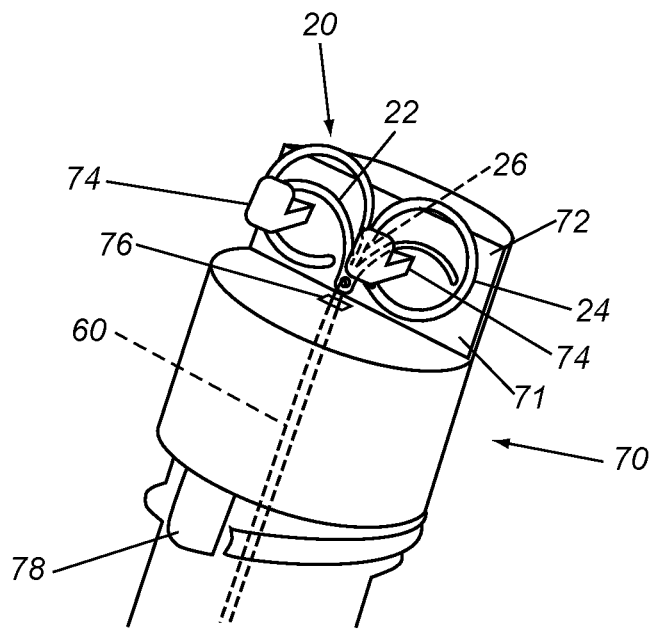
Figure 3D:
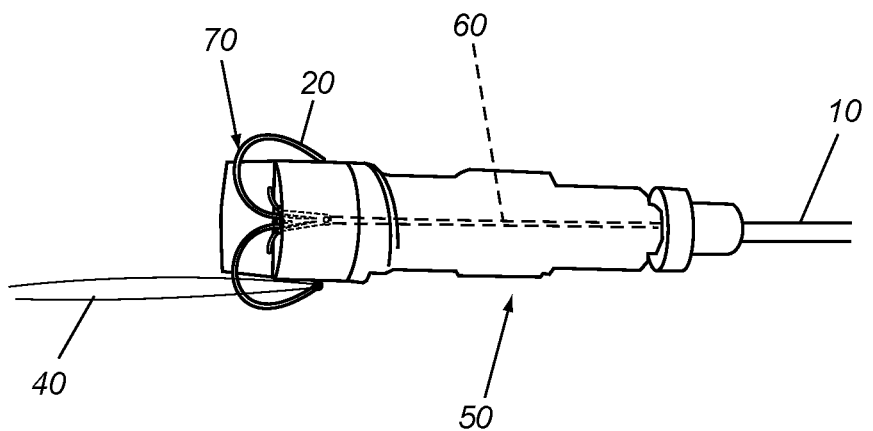

The clip 20 may be mounted to the loader 70 before or after directing the loading wire 60 through the hole 28. For example, as shown in FIG. 3C, the loader 70 may include a recess 71 defining a planar surface 72 from which a pair of prongs 74 extend. The prongs 74 may be spaced apart such that the central region 26 of the clip 20 may be positioned between the prongs 74 and the proximal tines 24 at least partially surround respective prongs 74. In addition, the loader 70 includes a slot or passage 76 that extends distally from the recess 71 towards a distal end 78 of the loader 70, the slot 76 having a cross-sectional shape, e.g., an oblong shape, corresponding to the shape of the lumen 16 of the needle 10. The loader 70 may be formed from substantially rigid material, e.g., metal, plastic, or composite material, for example, by molding, casting, machining, and the like.

During loading, the clip 20 may be placed in the relaxed state against the planar surface 72 with the central region 26 between the prongs 74 and the prongs 74 extending through the open region defined by the proximal tines 24 adjacent the distal tines 22. The prongs 74 may include flanges, hooks, or other features that engage the proximal tines 24 to prevent the tines from moving out of plane, i.e., away from the planar surface 72 during subsequent loading and/or other manipulation, while allowing the tines 22, 24 to slide around the prongs 74 within the plane.

In one embodiment, the ends of the loading wire 60 (not shown in FIG. 3C) may be directed through the slot 76 of the loader 70 before and/or during mounting of the clip 20 to the loader 70. Alternatively, after mounting the clip 20 to the loader 70, one end of the loading wire 60 may be directed through the slot 76 from the distal end 78, through the hole 28 and back into the slot 76 such that both ends of the loading wire 60 are located outside and distal to the distal end 78 of the loader 70. Similarly, the release wire 40 may be directed through the eyelet 27 in one of the proximal tines 24 before or after mounting the clip 20 to the loader 70.

The ends of the loading wire 60 may be introduced into the lumen 16 of the needle 10, e.g., through the hub 50 into the proximal end 12 until the ends exit the outlet 17 at the distal end 14 (not shown). The distal end 78 of the loader 70 may then be mounted to the hub 50 on the proximal end 12 of the needle 10, thereby aligning the slot 76 through the loader 70 with the lumen 16 of the needle 10. In an exemplary embodiment, the distal end 78 of the loader 70 may have a predetermined cross-sectional shape that ensures that the loader 70 is mounted to the hub 50 in the necessary orientation to align the major axes of the slot 76 and lumen 16. In addition or alternatively, the distal end 78 and/or hub 50 may include one or more cooperating elements that secure the loader 70 to the hub 50 in the desired orientation. Thus, with the loader 70 mounted to the hub 50, the central region 26 of the clip 20 and the slot 76 may be axially aligned with the longitudinal axis 18 of the needle and lumen 16.

The loading wire 60 may then be manipulated, e.g., by pulling both ends of the loading wire 60, to direct the clip 20 into and through the slot 76 in the loader 60 and into the lumen 16 of the needle 10. During this manipulation, the proximal and distal tines 24, 22 may be directed to the stressed state, e.g., where the proximal and distal tines 24, 22 are at least partially straightened and aligned with the central region 26, as shown in FIG. 1. For example, the prongs 74 of the loader 70 may allow first the distal tines 22 and then the proximal tines 24 to slide along the prongs 74 to compress them inwardly as they enter the slot 76. The loading wire 60 may continue to be pulled until the clip 20 is positioned at a desired location within the lumen 16, e.g., within the distal end 14 adjacent the outlet 17. As the clip 20 is pulled along the lumen 16, the release wire 40 may be pulled through the slot 76 into the lumen 16 following the proximal tine 24a having the eyelet 27.

Once the clip 20 is positioned within the lumen 16, the loader 70 may be disengaged and/or removed from the hub 50. For example, any connectors may be disengaged and the loader 70 withdrawn over the ends of the release wire 40 until fully removed. In addition, once the clip 20 is positioned at the desired location, the loading wire 60 may also be removed, e.g., by pulling one end to cause the other end to pass into the outlet 17 of the lumen 16, through the hole 28 and back out the outlet 17, thereby releasing the clip 20 constrained within the needle 10.

Once the clip 20 is loaded into the needle 10, any final assembly of the apparatus 8 may then be completed. For example, returning to FIG. 1, a pusher member 30 and valve member 54 may be coupled to the hub 50 after loading the clip 20 within the lumen 16. The valve member 54 may include a valve housing containing on or more seals therein, e.g., a hemostatic valve (not shown), which may provide a substantially fluid-tight seal, while accommodating axial movement of the pusher member 30 through the valve member 54 and hub 50.

The valve member 54 may be permanently or removably coupled to the proximal end 50a of the hub 50, e.g., using one or more of an interference fit, mating connectors, bonding with adhesive, sonic welding and the like. Alternatively, the valve member 54 may be integrated into the hub 50, e.g., by providing one or more valves within the proximal end 50a.

The pusher member 30 is an elongate member including a proximal end 32 disposed proximal to the hub 50 and valve member 54 and a distal end 34 that is sized to be slidably received within the lumen 16. For example, the pusher member 30 may have a length corresponding to the length of the needle 10 such that the distal end 34 is disposed immediately proximal and adjacent to the proximal tines 24 of the clip 20. The proximal end 32 may extend a sufficient distance proximally out of the valve member 54 such that the pusher member 30 may be directed distally from an initial or first position to one or more distal positions during deployment of the clip 20, as described further elsewhere herein.

The pusher member 30 and/or lumen 16 may be sized to accommodate the release wire 60 passing alongside the pusher member 30 within the lumen 16. For example, the pusher member 30 may be sized smaller than the lumen 16 such that the ends of the release wire 60 may be simply be disposed adjacent the pusher member 30 within the lumen 16. Alternatively, one or both of the pusher member 30 and lumen wall may include an axial groove to receive the release wire 60. In a further alternative, the pusher member 30 may include a passage (not shown) extending between the proximal and distal ends 32, 34 that may receive the release wire 60 therethrough.

During assembly, one or both ends of the release wire 40 may be directed through the valve member 54, e.g., through a valve passage and the one or more valves (not shown), such that the valve member 54 may be coupled to a proximal end 50a of the hub 50, as shown in FIG. 1. For example, in one embodiment, a first end 40a of the release wire 40 may be engaged between the hub 50 and valve member 54 to prevent subsequent movement of the first end 40a, while a second end 40b of the release wire may be directed through the valve member 54 such that the second end 40b extends proximally from the valve member 54 and is free to move. In this embodiment, the valve member 54 may be removably coupled to the hub 50 such that the valve member 54 may be removed to release the first end 40a of the release wire 40.

Alternatively, both ends of the release wire 40 may pass through the valve member 54 and be free to move. In this embodiment, the valve member 54 may be substantially permanently or removably attached to the proximal end 50a of the hub, as desired. In a further alternative, one or both ends of the release wire 40 may be coupled to an actuator (not shown) on the hub 50 to allow manipulation and release of the release wire 40, as described further below.

Optionally, as shown in FIG. 1, the hub 50 may include a side port 52 communicating with the lumen 16. The side port 52 may include one or more connectors, e.g., a Luer fitting (not shown), that may be used to couple a source of fluid to the side port 52. For example, a section of tubing 58 may be coupled to the side port 52 that communicates with a syringe (not shown) containing saline or other biocompatible liquid, which may be delivered from the syringe through the tubing 58 and side port 52 into the lumen 16 during use, as desired. The tubing 58 may be coupled to the side port 52 by cooperating connectors or, alternatively, may be substantially permanently attached to the side port 58, e.g., by one or more of an interference fit, mating connectors, bonding with adhesive, sonic welding, and the like.

In addition or alternatively, the hub 50 and/or valve member 54 may include one or more additional features to facilitate use of the apparatus 8. For example, if desired, one or more visual markers and/or other features (not shown) may be provided at desired locations around the periphery of the hub 50 and/or valve member 54, e.g., to provide a visual indication of the orientation of the clip 20 within the lumen 16 of the needle 10. For example, in one embodiment, the hub 50 may have an oblong shape, e.g., such that a major axis of the hub 50 is ninety degrees offset from the major dimension of the lumen 16. In addition or alternatively, one or more colored or other markers or elements (not shown) may be provided on the hub 50, e.g., on opposite sides of the hub 50 aligned with the minor dimension of the lumen 16 to define the plane of the clip 20 relative to the needle 10.

Optionally, the apparatus 8 may include a removable stop, e.g., disposed around the proximal end 32 of the pusher member 30, e.g., adjacent the valve member 54. For example, in one embodiment, the stop may be a "C" shaped collar or other element (not shown) that extends at least partially around the pusher member 30 and has a predetermined length to limit advancement of the pusher member 30. In the proximal or first position shown in FIG. 1, the clip 20 may be disposed entirely within the lumen 16, e.g., such that distal tines 22 of the clip 20 are disposed within and/or adjacent the distal tip 15 of the needle 10.

The pusher member 30 may be advanceable to a second or distal position, e.g., to deploy the distal tines 22 of the clip 20 from the lumen 16 beyond the distal tip 15 while the proximal tines 24 remain within the lumen 16. For example, the pusher member 30 may be advanced until the plunger stem 33 on the pusher member 30 abuts the stop, thereby preventing further advancement of the pusher member 30. The length of the stop may correspond to deploying a distal portion of the clip 20, e.g., the distal tines 22 beyond the distal tip 15, such that the distal tines 22 resiliently return at least partially towards the relaxed state.

The stop may be removable from around the pusher member 30, whereupon the needle 10 may be retracted proximally, e.g., equivalent to advancing the pusher member 30, until the pusher member 30 is in a third position relative to the needle 10, e.g., in which the entire clip 20 is deployed from the lumen 16 beyond the distal tip 15 of the needle 10. As the proximal tines 24 are deployed from the lumen 16, they may also resiliently return towards the relaxed state, thereby surrounding or otherwise engaging the tubular structure to be closed, as described further elsewhere herein.

Alternatively, the hub 50 and/or pusher member 30 may include a cooperating track (not shown) to control or limit movement of the pusher member 30 relative to the needle 10. For example, the track may include a first axial section allowing the pusher member 30 to be advanced axially from the first position to the second position, thereby partially deploying the clip 20, e.g., the distal tines 22. When desired to fully deploy the clip 20, the pusher member 30 may then be partially rotated, e.g., to move the pusher member 30 along a circumference (non-axial) section of the track, and then advanced axially along a third axial section to direct the pusher member 30 and needle 10 from the second position to the third position. Optionally, in this alternative, the hub 50 and/or pusher member 30 may include one or more markers (not shown) that may provide visual confirmation when the pusher member 30 is properly aligned along the track, e.g., sufficiently rotated to allow movement between the second and third positions.

Once assembled, the apparatus 8 may be further processed as desired, e.g., sterilized and packaged. The apparatus 8 may then be sold and/or otherwise provided to a doctor or other end-user who may use the apparatus 8 to deliver the clip 20 into a patient's body.

Figure 4A:
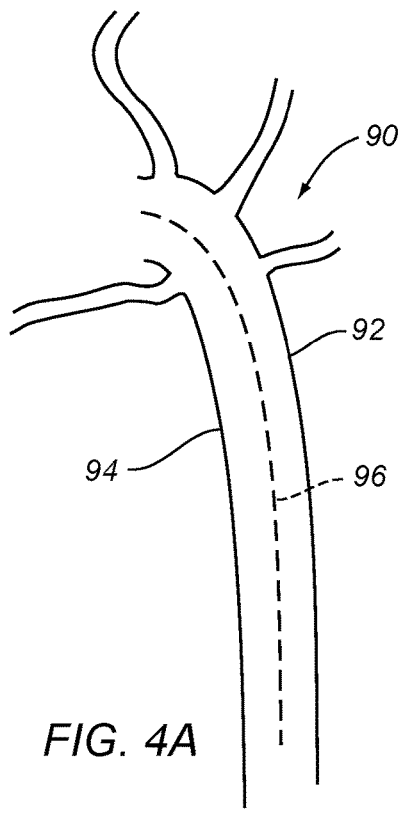

Turning to FIGS. 4A-4F, an exemplary method is shown for using the apparatus 8 of FIG. 1. Initially, as shown in FIG. 4A, a location along a vein or other body lumen 90, e.g., an anterior side 92 of the vein 90 closest to the skin (not shown), may be identified as a target location for delivering a clip 20, e.g., a saphenous vein experiencing valvular incompetence and the like. Optionally, a mark (not shown) may be applied to the patient's skin above the target location, e.g., to identify a point of entry for the needle 10. A local anesthetic may be injected or otherwise delivered to the skin and/or underlying tissue, e.g., between the skin and vein and/or around the vein, optionally, using the needle 10, as described elsewhere herein.

Figure 4B:
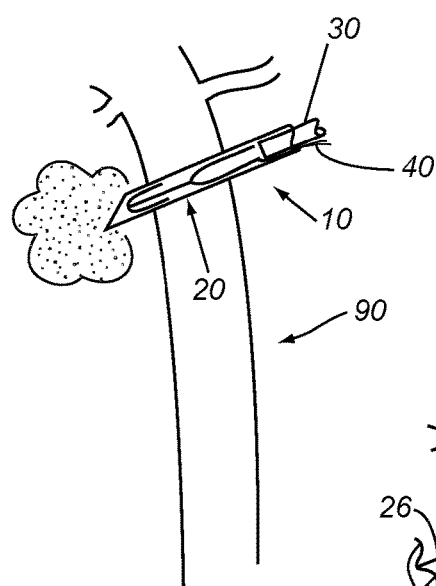

Turning to FIG. 4B, the needle 10 may be inserted through the skin and the point of entry and passed into-and-through the vein 90 such that the tip 15 is disposed on a posterior side 94 of the vein 90, e.g., using ultrasound visual control, as shown in FIG. 5A. The distal tip 15 of the needle 10 may be positioned beyond the posterior or inner wall 94 of the vein 90, e.g., about one or two millimeters (1-2 mm) deep beyond the posterior wall 92 of the vein 90.

Optionally, as shown in FIG. 4B, fluid may be delivered through the needle 10, e.g., from a syringe or other source (not shown) coupled to the side port 52 (see FIG. 1), thereby delivering the fluid through the lumen 16 and out the distal tip 15, into the region adjacent the vein 90. For example, such fluid may direct tissue surrounding the tubular structure away from the outer wall of the vein 90 and/or create a working space around the vein 90 to accommodate deployment of the distal tines 22. In exemplary embodiments, the fluid may simply be saline, or may include an anesthetic with vasoactive agent, such as lidocaine with epinephrine, which may be injected around the vein 90 to induce small muscle contraction or vasospasm, e.g., causing the vein 90 to contract around the needle 10 after being pierced through the vein 90. Optionally, such fluid may be delivered into the region adjacent to the vein 90, e.g., at one or more times during the procedure.

The orientation of the clip 20 may be checked, e.g., using one or more markers or other features on the hub 50 and/or valve member 54. For example, the needle 10 may be rotated about its longitudinal axis to ensure that the tines 22, 24 of the clip 20 may be oriented across the width of the vein 90, e.g., with the plane of the clip 20 substantially perpendicular to the longitudinal axis 96 of the vein 90.

Figure 4C:
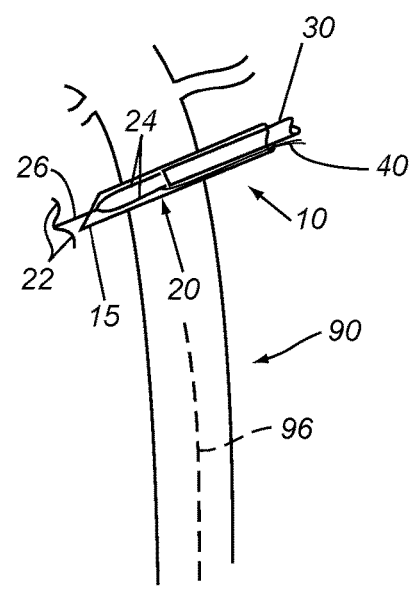

The pusher member 30 may be advanced until the distal tines 22 of the clip 20 exit the distal tip 15 of the needle 10, whereupon the distal tines 22 may expand automatically towards their relaxed state, as shown in FIG. 4C. For example, the pusher member 30 may be advanced until the plunger stem 33 contacts a stop (not shown) or is otherwise limited to a second position where the central region 26 and proximal tines 24 remain within the lumen 16. Optionally, anesthetic with vasoactive agent or other fluid may be delivered into the region adjacent to the vein 90, e.g., just before deployment of the distal tines 22, as shown in FIG. 4B.

Turning to FIG. 4D, once the distal tines 22 are deployed and expanded, the release wire 40 may be manipulated to direct the clip 20 proximally, e.g., to engage the distal tines 22 with the posterior side 94 of the vein 90. For example, the release wire 40 may be pulled at least partially proximally to engage the distal tines 22 with the posterior wall 94 of the vein 90, e.g., to prevent migration of the clip 20 during subsequent deployment and/or may partially compress or close the vein 90, as shown in FIG. 4C. Optionally, anesthetic with vasoactive agent or other fluid may be delivered into the region adjacent to the vein 90, e.g., after deploying the distal tines 22 and pulling outwardly on the release wire 40. Such fluid may create additional working space around the vein 90, e.g., to accommodate deployment of the proximal tines 24, e.g., as shown in FIG. 4E.

For example, if both ends of the release wire 40 are free, both ends may be pulled simultaneously to pull the intermediate region and consequently the clip 20 proximally. Alternatively, if one end of the release wire 40 is fixed, e.g., between the hub 50 and valve member 54, the other end may be pulled. Further alternatively, if the release wire 40 is coupled to an actuator (not shown), the actuator may be manipulated to pull the release wire 40 to a desired extent.

Once the distal tines 22 are engaged as desired with the vein 90, the release wire 40 may be removed from the eyelet 27 of the proximal tine 24a (not shown in FIG. 4C) to allow full deployment of the clip 20. For example, if both ends of the release wire 40 are free, one end may be pulled to direct the other end distally into the lumen 40, through the eyelet 27, and proximally back out through the lumen 40. Alternatively, if one end is fixed between the hub 50 and valve member 54, the valve member 54 may be disengaged to release the fixed end, whereupon the other end may be pulled to remove the release wire 40.

Turning to FIG. 4F, the entire needle 10 and pusher member 30 may then be removed through the vein 90 overlying tissue and skin, thereby deploying the clip 20 fully from the lumen 16. For example, with the distal tines 22 engaged to the posterior side 94 of the vein 90, removing the needle 10 may cause the proximal tines 24 to exit the outlet 17 and become exposed, whereupon the proximal tines 24 may automatically move towards the relaxed state, e.g., the loop shape shown in FIGS. 2A-2C, thereby at least partially surrounding, compressing, and/or closing the vein 90.

In an alternative embodiment, if the apparatus 8 includes a stop, the stop may be removed as the needle 10 and pusher member 30 are held substantially steadily in place. The needle 10 may then be withdrawn as the pusher member 30 is held or otherwise remains substantially stationary, thereby moving between the second and third positions, to push the proximal tines 24 of the clip 20 out the outlet 17.

Optionally, this procedure may be repeated one or more times, e.g., at the same location and/or different locations along the length of the vein 90, to deliver multiple clips (not shown) to close the vein 90.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for closing a tubular structure within a patient's body, comprising:
   a tubular member comprising a proximal end including a hub, a distal end including a sharpened distal tip to allow insertion into tissue through the tubular structure, and a lumen extending proximally from the distal end;
   a clip loaded in the lumen, the clip compressible between a relaxed state in which a plurality of tines of the clip are shaped to engage and close the tubular structure within a patient's body, and a stressed state in which the plurality of tines are compressed to allow the clip to be loaded into the lumen, the plurality of tines comprising a set of proximal tines and a set of distal tines, the plurality of tines disposed within the lumen compressed together in the stressed state, only one proximal tine of the set of proximal tines including an eyelet;

a release wire including first and second ends positioned adjacent the hub and an intermediate region passing through the lumen and the eyelet;

a pusher member comprising a proximal end and a distal end sized for advancement within the lumen for at least partially deploying the clip from the distal tip of the tubular member such that the plurality of tines engage and close the tubular structure through which the tubular member is directed, the pusher member movable relative to the tubular member from a first position to a second position wherein the distal tines are deployed from the lumen beyond the distal tip, the distal tines resiliently returning towards the relaxed state to at least partially engage the tubular structure through which the distal end of the tubular member is directed; and an actuator coupled to the release wire actuatable to direct the clip proximally after deploying the distal tines while the proximal tines remain within the lumen to enhance engagement of the distal tines around a posterior wall of the tubular structure.

2. The apparatus of claim 1, wherein the release wire is removable from the eyelet to allow the proximal tines to be deployed from the lumen, whereupon the proximal tines resiliently return towards the relaxed state to further engage the tubular structure to close the tubular structure.

3. The apparatus of claim 2, wherein the release wire is removable from the eyelet by pulling the first end of the release wire, the second end free to pass through the eyelet to release the proximal tines.

4. The apparatus of claim 2, wherein the first end of the release wire is coupled to the hub and the second end of the release wire is free to pass through the eyelet when the tubular member is removed to deploy the proximal tines from the lumen.

5. The apparatus of claim 1, wherein the tubular member is movable axially relative to the pusher member from the second position to a third position to deploy the entire clip from the lumen beyond the distal tip and remove the release wire from the eyelet, the proximal tines resiliently returning towards the relaxed state to further engage the tubular structure to close the tubular structure.

6. The apparatus of claim 5, further comprising a stop coupled between the pusher member and the hub to limit movement of the pusher member relative to the tubular member between the first and second positions.

7. The apparatus of claim 6, wherein the stop is removable from at least one of the pusher member and the hub to allow movement of the tubular member relative to the pusher member from the second position to the third position.

8. The apparatus of claim 1, wherein the distal tines are shorter than the proximal tines.

9. The apparatus of claim 8, wherein each of the proximal tines defines a loop within a plane in the relaxed state that at least partially surrounds a respective distal tine.

10. The apparatus of claim 1, wherein the set of distal tines comprise a pair of distal tines extending from a first end of a central region of the clip and the set of proximal tines comprise a pair of proximal tines extending from a second end of the central region.

11. The apparatus of claim 10, wherein the distal tines, proximal tines, and the central region define a plane in the relaxed state.

12. The apparatus of claim 11, wherein the distal and proximal tines remain substantially within the plane when the plurality of tines are compressed into the stressed state.

13. The apparatus of claim 10, wherein the distal tines are substantially shorter than the proximal tines.

14. The apparatus of claim 13, wherein each of the proximal tines defines a loop within a plane in the relaxed state that at least partially surrounds a respective distal tine.

15. The apparatus of claim 10, wherein the distal tines extend from the central region to define opposing hook shapes in the relaxed state and wherein the proximal tines extend from the central region such that the proximal tines at least partially surround the central region and the distal tines within the plane in the relaxed state.

16. The apparatus of claim 15, wherein the proximal tines and the distal tines are substantially straightened such that the proximal tines are axially aligned with the central region in the stressed state when the clip is loaded within the lumen.

17. The apparatus of claim 10, further comprising a hole in the central region adjacent the distal tines for receiving a loading wire to load the clip into the lumen.

18. The apparatus of claim 1, wherein:
the actuator is configured to remove the release wire from the eyelet to allow the proximal tines to be deployed from the lumen, and
the pusher member is moveable from the second position to a third position to deploy the proximal tines from the distal tip after removing the release wire, whereupon the proximal tines resiliently return towards the relaxed state to further engage the tubular structure to close the tubular structure.

19. An apparatus for closing a tubular structure within a patient's body, comprising:
a) a clip comprising:
  i) a central region including a proximal end and a distal end, the distal end including a hole for receiving a loading wire;
  ii) a pair of distal tines extending from the distal end, the distal tines biased to extend away from one another in a relaxed state; and
  iii) a pair of proximal tines extending from the proximal end, the proximal tines having a length greater than a length of the distal tines, the proximal tines defining loops in a relaxed state that at least partially surround respective distal tines within a plane, only one of the proximal tines including an eyelet adjacent a tip thereof; and
b) a delivery device comprising:
  i) a tubular member comprising a proximal end including a hub, a distal end including a sharpened distal tip such that the tubular member may be directed into tissue through a tubular structure within a patient's body, and a lumen extending proximally from an outlet in the tubular member distal end, the clip loaded within the lumen in a stressed state wherein the proximal tines and distal tines are substantially straightened and axially aligned with the central region;
  ii) a pusher member within the lumen movable relative to the tubular member from a first position to a second position to deploy the distal tines initially from the outlet, the distal tines resiliently returning towards their relaxed state;

iii) a release wire including first and second ends and an intermediate region received through the eyelet; and iv) an actuator coupled to the release wire to direct the clip proximally relative to the tubular member distal end while the proximal tines remain within the lumen to engage the distal tines with a posterior wall of the tubular structure, the actuator configured to remove the release wire from the eyelet while the proximal tines remain within the lumen to allow the proximal tines to be deployed from the lumen, the pusher member movable from the second position to a third position after the release wire is removed to deploy the proximal tines from the distal tip, whereupon the proximal tines resiliently return towards their relaxed state to at least partially surround and close the tubular structure.

20. A method for closing a tubular structure within a patient's body, comprising:

inserting a distal tip of a delivery device into the patient's body into-and-through the tubular structure, the delivery device carrying a clip including a set of distal tines and a set of proximal tines in a stressed state and a release wire coupled to only one of the proximal tines;

partially deploying the clip such that the distal tines of the clip extend from the distal tip beyond the tubular structure and elastically deform towards a relaxed state while the proximal tines remain within the distal tip;

actuating the release wire to direct the distal tines proximally into engagement with a posterior wall of the tubular structure while the proximal tines remain within the distal tip;

disengaging the release wire from the one of the proximal tines while the proximal tines remain within the distal tip; and after disengaging the release wire, fully deploying the clip from the delivery device such that the proximal tines are released from the distal tip and elastically deform to at least partially surround and close the tubular structure.

21. The method of claim 20, wherein the release wire is received through an eyelet in the only one of the proximal tines, and wherein the release wire is disengaged by pulling a first end of the release wire until a second end of the release wire passes through the eyelet to release the one of the proximal tines.

22. The method of claim 21, wherein fully deploying the clip comprises moving the tubular member axially relative to a pusher member to deploy the entire clip from the distal tip and remove the release wire from the eyelet, the proximal tines resiliently returning towards the relaxed state to at least partially surround and close the tubular structure.

23. The method of claim 20, wherein the release wire is received through an eyelet in the only one of the proximal tines, the release wire including a first end coupled to the hub and a second free end, and wherein disengaging the release wire comprises withdrawing the tubular member at least partially from the patient's body, thereby causing the second free end of the release wire to pass through the eyelet to release the one of the proximal tines.

24. The method of claim 23, wherein the clip is fully deployed from the lumen when the tubular member is withdrawn from the patient's body after disengaging the release wire.

* * * * *